United States Patent
Italiaie (10) Patent No.: US 11,350,922 B1
(45) Date of Patent: Jun. 7, 2022

(54) MODULAR SURGICAL INSTRUMENT SYSTEM AND METHOD FOR SHANK-BASED RETRACTION AND DISTRACTION

(71) Applicant: Warsaw Orthopedic, Inc., Warsaw, IN (US)

(72) Inventor: Christel Italiaie, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/166,265

(22) Filed: Feb. 3, 2021

(51) Int. Cl.
*A61B 17/02* (2006.01)

(52) U.S. Cl.
CPC ........ *A61B 17/025* (2013.01); *A61B 17/0206* (2013.01)

(58) Field of Classification Search
CPC .......................... A61B 17/025; A61B 17/0206
USPC ........ 600/210, 213, 214, 215, 216, 217, 219
See application file for complete search history.

(56) References Cited

U.S. PATENT DOCUMENTS

| | | | |
|---|---|---|---|
| 5,928,139 A * | 7/1999 | Koros | A61B 17/0206 600/205 |
| 6,206,826 B1 * | 3/2001 | Mathews | A61B 17/025 600/210 |
| 6,945,933 B2 | 9/2005 | Branch et al. | |
| 7,011,658 B2 | 3/2006 | Young | |
| 7,494,463 B2 | 2/2009 | Nehls | |
| 7,578,822 B2 | 8/2009 | Rezach et al. | |
| 7,618,424 B2 | 11/2009 | Wilcox et al. | |
| 7,976,463 B2 | 7/2011 | Dewey et al. | |
| 8,157,809 B2 | 4/2012 | Butters et al. | |
| 8,162,952 B2 | 4/2012 | Cohen et al. | |
| 8,172,750 B2 | 5/2012 | Miles et al. | |
| 8,317,692 B2 | 11/2012 | Loftus et al. | |
| 8,357,184 B2 | 1/2013 | Woolley et al. | |
| 8,435,269 B2 | 5/2013 | Woolley et al. | |
| 8,439,832 B2 | 5/2013 | Miles et al. | |
| 8,460,310 B2 | 6/2013 | Stern | |
| 8,506,574 B2 | 8/2013 | Butters et al. | |
| 8,535,320 B2 | 9/2013 | Woolley et al. | |
| 8,562,521 B2 | 10/2013 | Miles et al. | |
| 8,602,982 B2 | 12/2013 | Miles et al. | |
| 8,636,655 B1 | 1/2014 | Childs | |
| 8,747,307 B2 | 6/2014 | Miles et al. | |

(Continued)

OTHER PUBLICATIONS

MAST QUADRANT™, Medial Lateral Blades Procedural Solutions Technique, Medtronic Sofamor Danek USA, Inc., 2006.

*Primary Examiner* — Eduardo C Robert
*Assistant Examiner* — David C Comstock
(74) *Attorney, Agent, or Firm* — Fox Rothschild LLP; P. Marshall Ticer (57) ABSTRACT

A surgical device includes at least one retractor blade. Each retractor blade includes a blade body having a lateral side, a medial side opposite the lateral side and a bottom end. The bottom end has an inverted-arch curvature. The inverted-arch curvature includes a lowest point in proximity to a midline of the blade body. Each retractor blade includes a connector integrated into a mid-section on the medial side of the blade body and a leg interface configured to mate and/or pair with a leg of a distractor. The at least one retractor blade may include two retractor blades configured as mirror images of each other. Each blade is configured to pair with a respective one distractor.

20 Claims, 9 Drawing Sheets

(56) References Cited

U.S. PATENT DOCUMENTS

| | | | |
|---|---|---|---|
| 8,852,089 B2 | 10/2014 | Blackwell et al. | |
| 8,894,573 B2 | 11/2014 | Loftus et al. | |
| 8,915,925 B2 | 12/2014 | Butters et al. | |
| 9,044,280 B1 | 6/2015 | Arambula et al. | |
| 9,050,146 B2 | 6/2015 | Woolley et al. | |
| 9,101,413 B2 | 8/2015 | Masson et al. | |
| 9,131,966 B2 | 9/2015 | Solitario, Jr. et al. | |
| 9,216,016 B2 | 12/2015 | Fiechter et al. | |
| 9,301,743 B2 | 4/2016 | Miles et al. | |
| 9,307,972 B2 | 4/2016 | Lovell et al. | |
| 9,345,463 B2 | 5/2016 | Butters et al. | |
| 9,414,828 B2 | 8/2016 | Abidin et al. | |
| 9,700,293 B2 | 7/2017 | Cryder et al. | |
| 9,795,370 B2 | 10/2017 | O'Connell et al. | |
| 9,962,147 B2 | 5/2018 | O'Connell et al. | |
| 10,039,539 B2 | 8/2018 | Friedrich et al. | |
| 10,092,283 B2 | 10/2018 | Cryder et al. | |
| 10,172,652 B2 | 1/2019 | Woolley et al. | |
| 10,194,958 B2 | 2/2019 | Bobbitt et al. | |
| 10,231,724 B1 | 3/2019 | Lovell et al. | |
| 10,278,687 B2 | 5/2019 | Cryder et al. | |
| 10,278,786 B2 | 5/2019 | Friedrich et al. | |
| 10,363,022 B2 | 7/2019 | Serokosz et al. | |
| 10,390,862 B2 | 8/2019 | Bobbitt et al. | |
| 10,405,842 B2 | 9/2019 | Kim | |
| 10,426,454 B2 | 10/2019 | Ponmudi et al. | |
| 10,470,752 B2 | 11/2019 | Butters et al. | |
| 10,499,896 B2 | 12/2019 | Abidin et al. | |
| 10,499,897 B2 | 12/2019 | Truckey | |
| 10,507,046 B2 | 12/2019 | Reitblat et al. | |
| 10,603,026 B2 | 3/2020 | Cryder et al. | |
| 10,660,628 B2 | 5/2020 | O'Connell et al. | |
| 10,660,631 B1 | 5/2020 | Boesel et al. | |
| 2005/0021040 A1* | 1/2005 | Bertagnoli | A61B 17/708 606/90 |
| 2005/0203533 A1 | 9/2005 | Ferguson et al. | |
| 2007/0100212 A1* | 5/2007 | Pimenta | A61N 1/0551 600/210 |
| 2010/0331849 A1 | 12/2010 | Riesinger et al. | |
| 2011/0098537 A1 | 4/2011 | Justis et al. | |
| 2011/0130793 A1* | 6/2011 | Woolley | A61B 17/7076 606/279 |
| 2011/0184245 A1* | 7/2011 | Xia | A61B 46/17 600/202 |
| 2011/0245836 A1* | 10/2011 | Hamada | A61B 17/0293 606/90 |
| 2013/0046147 A1 | 2/2013 | Nichter et al. | |
| 2014/0024900 A1 | 1/2014 | Capote et al. | |
| 2014/0031874 A1 | 1/2014 | Kucharzyk et al. | |
| 2014/0066718 A1* | 3/2014 | Fiechter | A61B 17/7077 600/214 |
| 2015/0257784 A1* | 9/2015 | Corbin | A61B 17/0293 600/210 |
| 2016/0345952 A1 | 12/2016 | Kucharzyk et al. | |
| 2017/0049428 A1 | 2/2017 | Cryder et al. | |
| 2017/0189080 A1* | 7/2017 | Reitblat | A61B 17/708 |
| 2018/0035990 A1 | 2/2018 | Eftekhar | |
| 2018/0153585 A1 | 6/2018 | Levine | |
| 2018/0206833 A1 | 7/2018 | O'Connell et al. | |
| 2018/0271507 A1 | 9/2018 | Gasser | |
| 2019/0008498 A1 | 1/2019 | McClymont et al. | |
| 2019/0216451 A1 | 7/2019 | Cryder et al. | |
| 2019/0231334 A1 | 8/2019 | Serokosz et al. | |
| 2019/0298327 A1 | 10/2019 | Serokosz et al. | |
| 2019/0350572 A1 | 11/2019 | Ponmudi et al. | |
| 2019/0388079 A1 | 12/2019 | Kim | |
| 2020/0054361 A1 | 2/2020 | Peultier et al. | |
| 2020/0093529 A1 | 3/2020 | Biedermann et al. | |
| 2020/0113606 A1 | 4/2020 | Reitblat et al. | |
| 2020/0113713 A1 | 4/2020 | LaMarca et al. | |
| 2020/0121310 A1 | 4/2020 | Butters et al. | |
| 2020/0245994 A1 | 8/2020 | O'Connell et al. | |
| 2020/0315602 A1* | 10/2020 | Melton | A61B 17/7001 |

* cited by examiner

MODULAR SURGICAL INSTRUMENT SYSTEM AND METHOD FOR SHANK-BASED RETRACTION AND DISTRACTION

FIELD

The present technology is generally related to systems and methods using modular retractor blade and distractors to provide retraction and distraction at the same time for use in a mini-open transforaminal lumbar interbody fusion (TLIF) spine surgery.

BACKGROUND

Spinal disorders may result in pain, nerve damage, and loss of mobility. While, non-surgical treatments may be effective to treat some spine disorders, others will require surgical treatments, such as without limitation, spinal fusions. During, a mini-open transforaminal lumbar interbody fusion (TLIF) spine surgery, an incision can be made off the midline to access both disc space and pedicles. Other spine surgeries may place the incision in a different location. Various tools are used to perform retraction with blades to expose a portion of the spine or boney structures through the incision. Other instruments are used to perform distraction. The interchange of these different instruments may increase the length of time required to perform the surgery. This disclosure describes methods and systems directed to addressing the problems described above, and/or other issues.

SUMMARY

The techniques of this disclosure generally relate, for example, to a modular surgical instrument system using modular retractor blade and distractors to provide retraction and/or distraction, which may be provided at the same time for use, for example, in an open, mini-open transforaminal lumbar interbody fusion (TLIF) spine surgery, or other applicable procedures.

In one aspect, the present disclosure provides a surgical device comprising at least one retractor blade. Each retractor blade may include a blade body having a lateral side, a medial side opposite the lateral side, and a bottom end. The bottom end may include an inverted-arch curvature. The inverted-arch curvature may include a lowest point in proximity to a midline of the blade body. Each retract blade may include a connector integrated into a mid-section on the medial side of the blade body. The connector may include a leg interface configured to mate with a leg of a distractor.

In another aspect, the disclosure provides a modular surgical instrument system that may include a medial-lateral distractor rack tool having first and second parallel arms. The modular surgical instrument system may include first and second leg-docking members connected to the first and second parallel arms. The modular surgical instrument system may include a first distractor having a first distractor leg configured to be docked with the first leg-docking member. The modular surgical instrument system may include a second distractor having a second distractor leg configured to be docked with the second leg-docking member. The modular surgical instrument system may include a retractor blade pair. Each retractor blade of the blade pair comprises a blade body having a lateral side, a medial side opposite the lateral side and a bottom end. The bottom end may include an inverted-arch curvature. The inverted-arch curvature may include a lowest point in proximity to a midline of the blade body. Each blade may include a connector integrated into a mid-section on the medial side of the blade body. The connector may include a leg interface configured to mate with the first distractor leg or the second distractor leg.

In another aspect, the disclosure provides a method that may include providing the modular surgical instrument system and driving a shank of a bone fastener into a pedicle. The method may include sliding a retractor blade over a distractor leg of a distractor to pair the retractor blade and distractor together and attaching in situ, the distractor to the shank of the bone fastener. The method may include attaching a medial-lateral distractor rack tool to the distractor leg to assemble the system and performing distraction and retraction with the assembled system using the paired retractor blade and the distractor.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The embodiments of a surgical instrument system are discussed in terms of medical devices for the treatment of musculoskeletal disorders and more particularly, in terms of a surgical instrument system and a method for treating a spine. In some embodiments, the system includes at least one modular surgical device with a retraction blade and distractor pair for both shank-based retraction and distraction and related methods of use that can create a distraction in the disc space while retracting fascia and/or muscles during spine surgery.

The disclosure is directed, for example, to surgical tools used to treat spinal disorders such as, for example, degenerative disc disease, disc herniation, osteoporosis, spondylolisthesis, stenosis, scoliosis and other curvature abnormalities, kyphosis, tumor and fractures.

The system of the present disclosure may be understood more readily by reference to the following detailed description of the embodiments taken in connection with the accompanying drawing figures that form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, front, back, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a modular surgical instrument system including at least one modular surgical device and related components and methods of employing the surgical instrument system in accordance with the principles of the present disclosure. Alternate embodiments are also disclosed. Reference is made in detail to the exemplary embodiments of the present disclosure, which are illustrated in the accompanying figures.

Figure 1A:
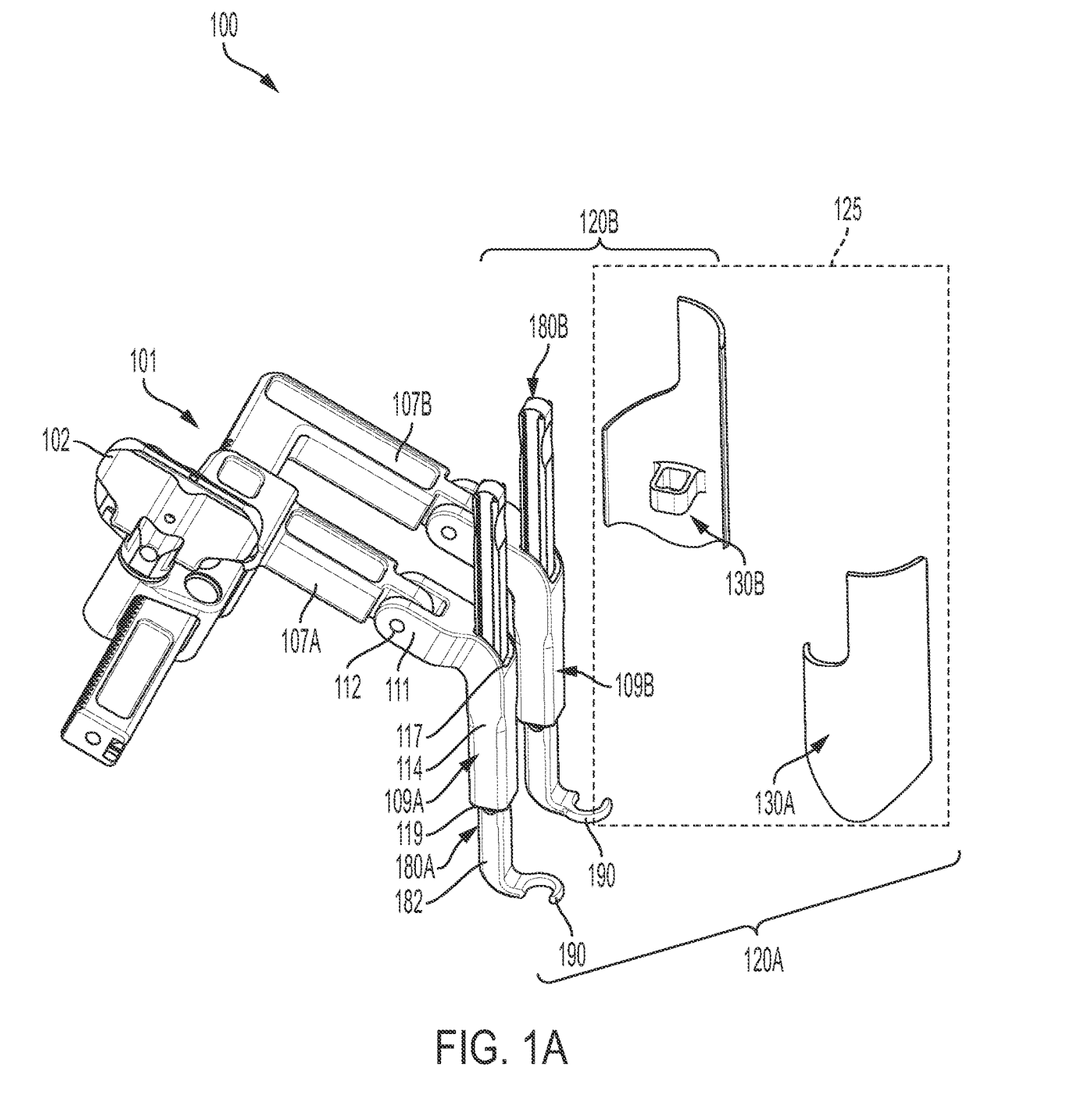
FIG. 1A is a perspective view that illustrates components of a modular surgical instrument system for shank-based retraction and distraction with the retraction blades separated.
Figure 1B:
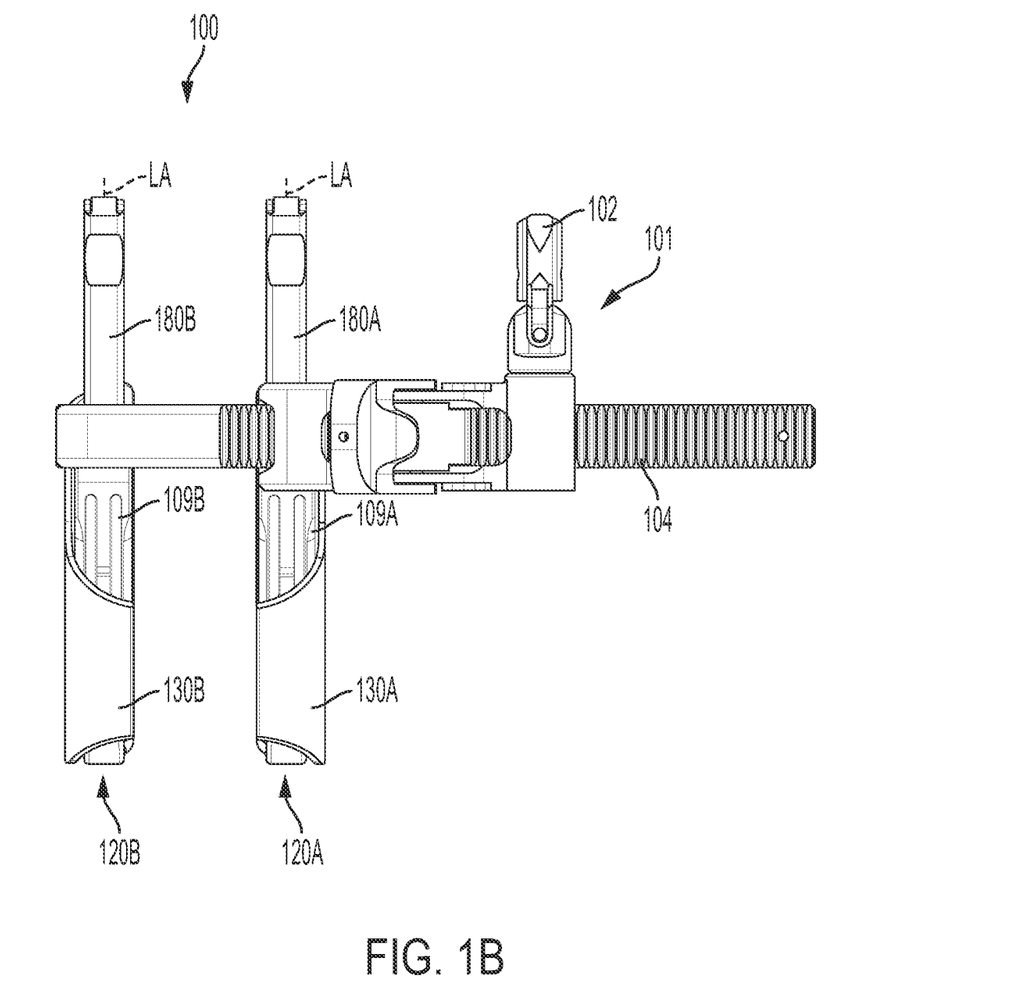
FIG. 1B is a rear view that illustrates the components of the modular surgical instrument system.

Turning to FIG. 1A, a perspective view that illustrates components of a modular surgical instrument system 100 for shank-based retraction and distraction with the retraction blades separated is shown. FIG. 1B is a rear view that illustrates the components of the modular surgical instrument system 100.

The components of the system 100 can be fabricated from biologically acceptable materials suitable for medical applications, including metals, synthetic polymers, ceramics and bone material and/or their composites. For example, the components of system 100, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologic Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of the system 100 may have material composites, including the above materials, to achieve various desired characteristics such as strength, rigidity, elasticity, compliance, biomechanical performance, durability and radiolucency or imaging preference. The components of the system 100, individually or collectively, may also be fabricated from a heterogeneous material such as a combination of two or more of the above-described materials. The components of the system 100 may be monolithically formed, integrally connected or include fastening elements and/or instruments, as described herein.

The system 100 may be employed, for example, with an open or mini-open, minimal access and/or minimally invasive including percutaneous surgical techniques. In one embodiment, the components of the system 100 may be configured to distract and/or retract to fix a bone fastener, such as a pedicle screw, for a surgical treatment to treat various spine pathologies, such as those described herein. The system 100 may be configured to create a distraction in the disc space while retracting fascia and/or muscles during spine surgery.

The bone fastener may include a head portion that defines an implant cavity and a penetrating portion or shank configured for penetrating tissue. As used in this disclosure, shank-based retraction may relate to, for example, to applying force to the shank or shaft, for example, associated with a bone fastener or may further relate to other posts, shafts, shanks or sleeves or other extensions implanted or embedded in a portion of the spine or other bony structures. The bone fastener may be coated with an osteoconductive material such as hydroxyapatite and/or osteoinductive agent such as a bone morphogenic protein for enhanced bony fixation. Bone fastener can be made of radiolucent materials such as polymers. Radiomarkers may be included for identification under x-ray, fluoroscopy, CT, or other imaging techniques. Metallic or ceramic radiomarkers, such as tantalum beads, tantalum pins, titanium pins, titanium endcaps, and platinum wires can be used.

It is contemplated that the present disclosure may be employed with other osteal and bone related applications, including those associated with diagnostics and therapeutics. It is further contemplated that the disclosed surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the thoracic, lumbar, sacral, cervical, and pelvic sections of the spinal column. The system 100 of the present disclosure may also be used on animals, simulated spinal bone models or other non-living substrates, such as, without limitations for use in testing and training.

Figure 2A:
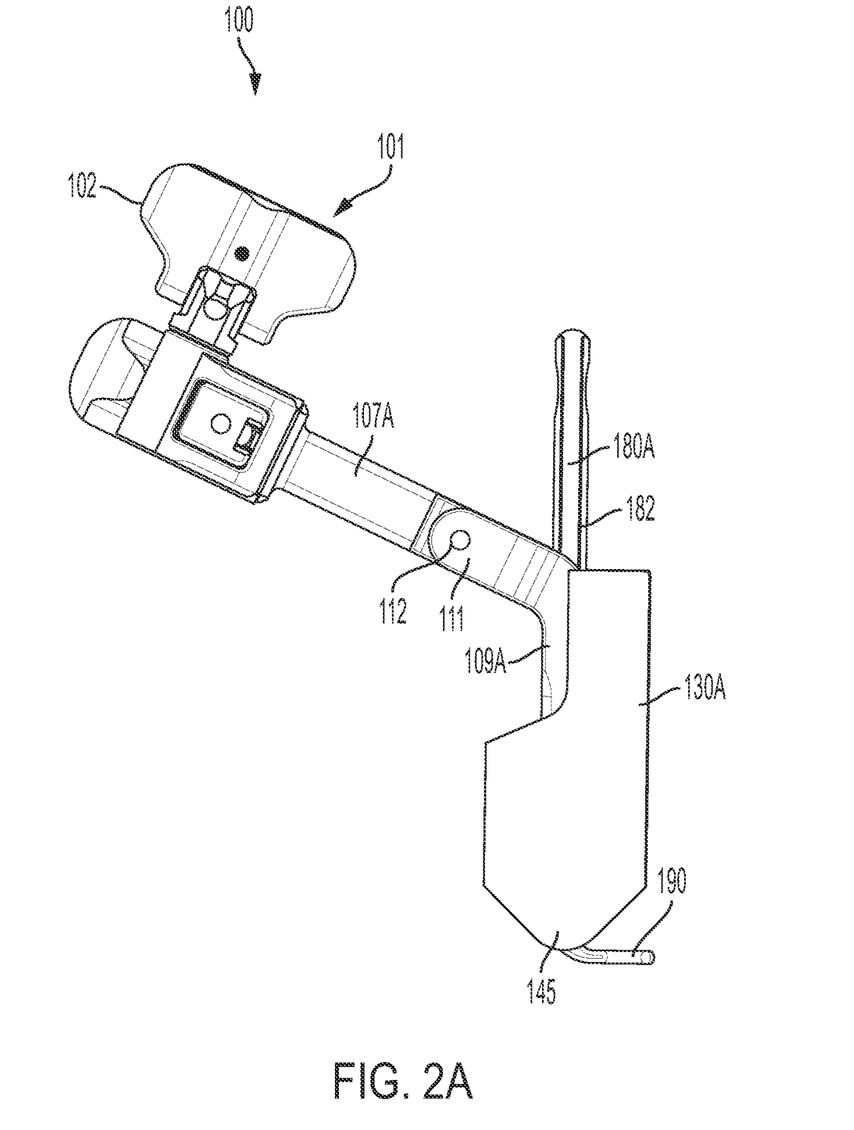
FIG. 2A is a lateral side view that illustrates the components of the modular surgical instrument system.
Figure 2B:
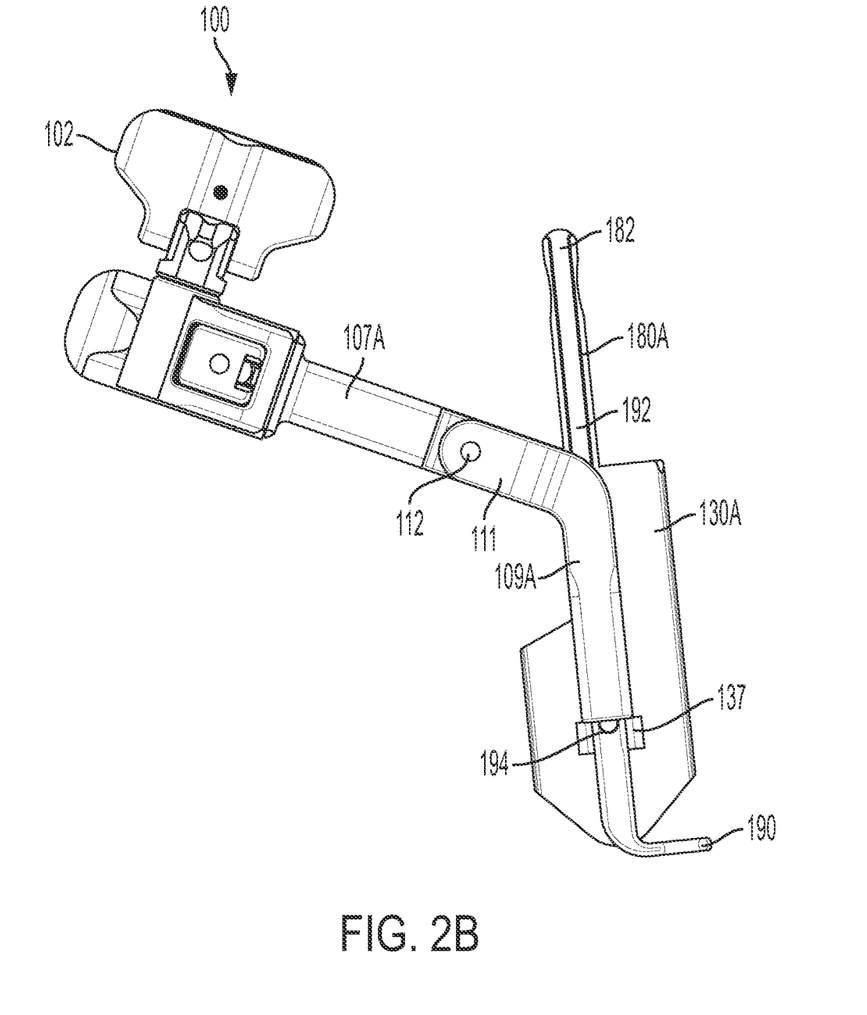
FIG. 2B is a medial side view that illustrates the components of the modular surgical instrument system.

The system 100 will be described in relation to FIGS. 1A-1B and FIGS. 2A and 2B. FIGS. 2A-2B are lateral side and medial side views that illustrate the components of the modular surgical instrument system 100. The modular surgical instrument system 100 may include a medial-lateral distractor rack tool 101 having first and second parallel arms 107A, 107B. The system 100 may include first and second leg-docking members 109A, 109B connected to the first and second parallel arms 107A, 107B.

The medial-lateral distractor rack tool 101 may include a knob 102 that may be configured to be rotated clockwise or counter-clockwise. Rotating the knob 102 in a first direction may close the tool 101 such that the spacing between the first and second parallel arms 107A, 107B is decreased. By way of non-limiting example, the first direction may be clockwise. Alternately, rotating the knob 102 in a second direction may open the tool 101 such that the spacing between the first and second parallel arms 107A, 107B is increased. By way of non-limiting example, the second direction may be counter-clockwise.

The medial-lateral distractor rack tool 101 may include a rack of teeth 104 (FIG. 1B) interfaced with the first and second parallel arms 107A, 107B so that as the knob 102 is rotated in the second direction, at least one of the arms moves relative to the other arm to increase the distance between the arms 107A, 107B. An example rack tool for retraction is described in U.S. Patent Application Publication 2014/0024900, titled "SURGICAL RETRACTOR AND METHOD OF USE," assigned to Warsaw Orthopedic, Inc., which is incorporated herein in its entirety. Another example, rack tool for retraction is described in U.S. Patent Application Publication 2011/0098537, titled "TISSUE MASSAGE RETRACTOR," to Warsaw Orthopedic, Inc., which is incorporated herein in its entirety. Another rack tool for retraction is described in U.S. Pat. No. 7,976,463, titled "INSTRUMENTS AND METHODS FOR MINIMALLY INVASIVE TISSUE RETRACTION AND SURGERY," assigned to Warsaw Orthopedic, Inc., which is incorporated herein by reference in its entirety. A rack tool for retraction is also described in U.S. Pat. No. 6,945,933, titled "INSTRUMENTS AND METHODS FOR MINIMALLY INVASIVE TISSUE RETRACTION AND SURGERY," assigned to SDGI Holding, Inc., which is incorporated herein by reference in its entirety.

Since each of the first and second leg-docking members 109A, 109B are essentially the same, only one leg-docking member 109A will be described. The leg-docking member 109A may include a yoke 111 and a connector pin 112 configured to connect to a respective one arm 107A. The yoke 111 of the leg-docking member 109B may be configured to connect to arm 107B. The first leg-docking member 109A may include a hollow tubular member 114 having a first end 117 integrated with the yoke 111 and a second end 119. The second end 119 is at an opposite the first end 117. The yoke 111 may be arranged at an angle relative to the first end 117 of the hollow tubular member 114. The angle between the hollow tubular member 114 and the yoke 111 may be 90° or an obtuse angle that may be less than 180°.

The system 100 may include at least modular surgical device 120A, 120B. The modular surgical device 120A may include a retractor blade 130A that may be a standalone retractor blade. The modular surgical device 120A may include a distractor 180A. The standalone retractor blade 130A may be paired with a distractor 180A to form a retractor blade and distractor pair. The retractor blade 130A may be paired with a distractor 180A with a connector 137 integrated into a medial side of the blade 130A. The system 100 may include a second modular surgical device 120B that may include a retractor 130B and distractor 180B. The retractor blade 130B may be paired with a distractor 180B with a connector 137 integrated into a medial side of the blade 130B.

In various embodiments, the distractors 180A and 180B may be essentially the same. Therefore, only one distractor 180A will be described in detail with additional distractor details provided in relation to FIG. 5. With reference specifically to FIGS. 1A and 1B, the distractor 180A may include a distractor leg 182 and hook 190. The leg 182 may be configured to be docked with the first leg-docking member 109A. The distractor leg 182 of distractor 180B may be configured to be docked with the second leg-docking member 109B. This docking may occur with the assistance of a robotic system and/or with the aid of surgical navigation techniques. The system 100 may include a plurality of distractors that may be selected to assist with distraction during spine surgery. By way of non-limiting example, distractors may have different hook types, as will be described in more detail in relation to FIGS. 5-6. The distractor leg 182 has a longitudinal axis LA (FIG. 1B).

In various embodiments, the system 100 may include a plurality of standalone retractor blades of different sizes that may be selected for a pairing with a distractor. For example, the retractor blades may have different longitudinal lengths, diameters or thicknesses. In various embodiments, the plurality of standalone retractor blades may include a retractor blade pair 125, denoted in the dashed box.

Figure 3A:
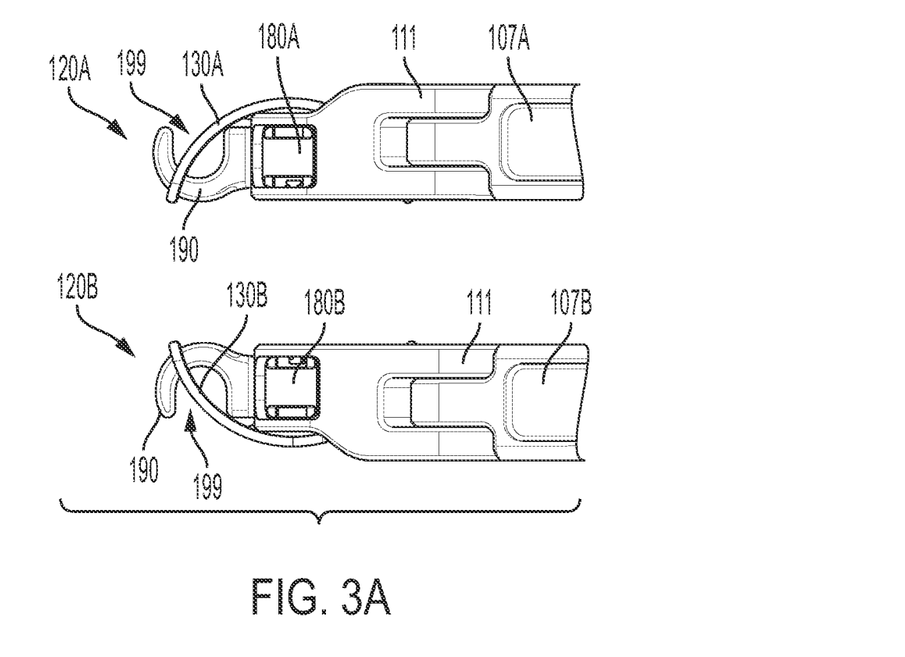
FIG. 3A is a top view of the modular surgical device installed in first and second leg-docking members.
Figure 3B:
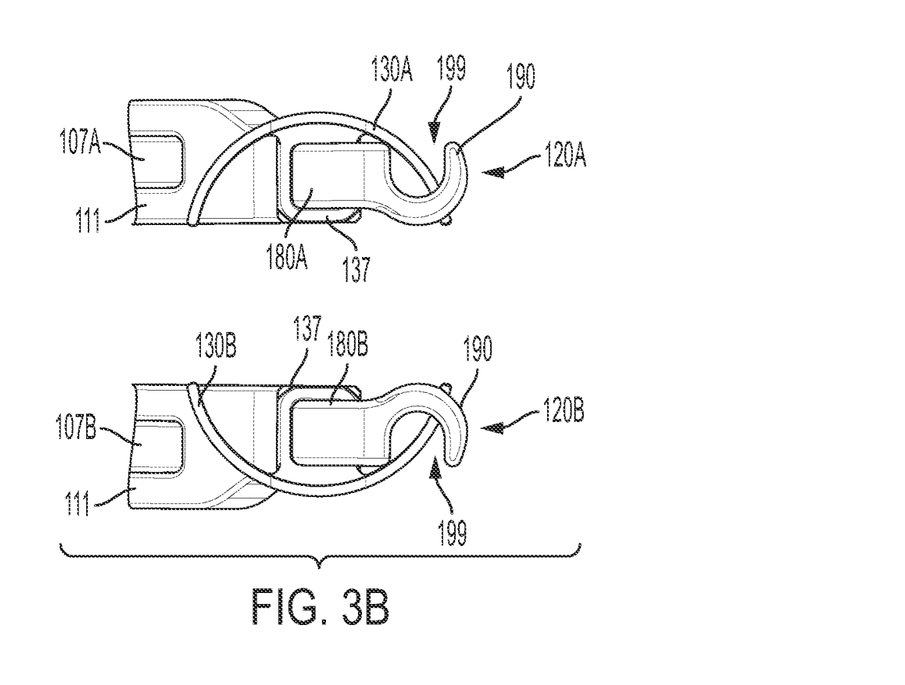
FIG. 3B is a bottom view of the modular surgical device installed in first and second leg-docking members.

FIG. 3A is a top view of the modular surgical devices 120A, 120B installed in first and second leg-docking members 109A, 109B. FIG. 3B is a bottom view of the modular surgical device 120A, 120B installed in the first and second leg-docking members 109A, 109B. The first and second leg-docking members 109A, 109B are shown attached to arms 107A, 107B. The retractor blade pair 125 may include a first retractor blade 130A and a second retractor blade 130B that is a mirror image of the first retractor blade 130A. The system 100 may be configured to position the medial sides of the first retractor blade 130A and a second retractor blade 130B facing each other. The hook 190 of the distractor 180A, 180B may have an opening 199 that may open in a direction toward the medial side of the retractor blade. Additionally, the hook 190 may be offset in a direction of a front side of the blade. In this disclosure, the term "front side" of the blade is in a direction that when installed is farthest from the tool 101. A retractor blade will be described in more detail in relation to FIGS. 4A-4D.

Figure 4A:
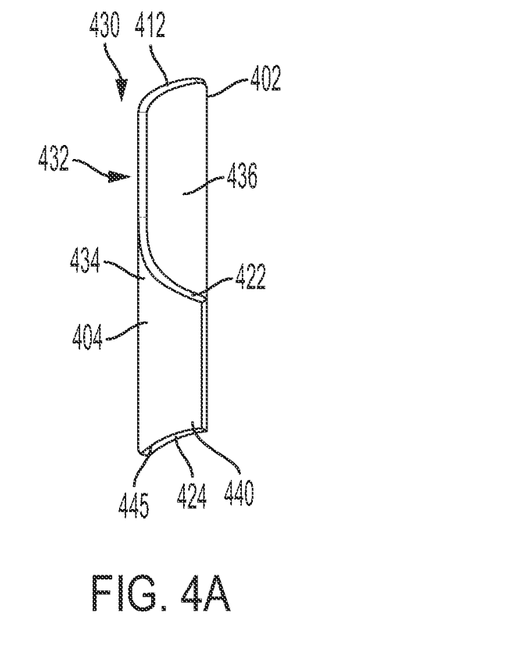
FIG. 4A is a rear view that illustrates the retractor blade.
Figure 4B:
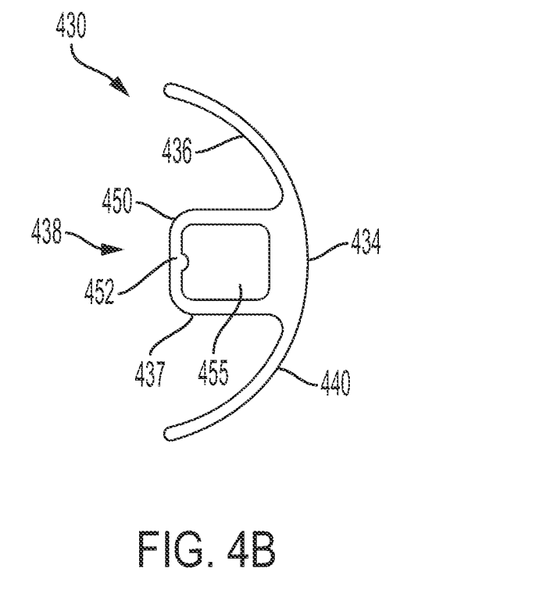
FIG. 4B is a bottom end view that illustrates the retractor blade of FIG. 4A.
Figure 4C:
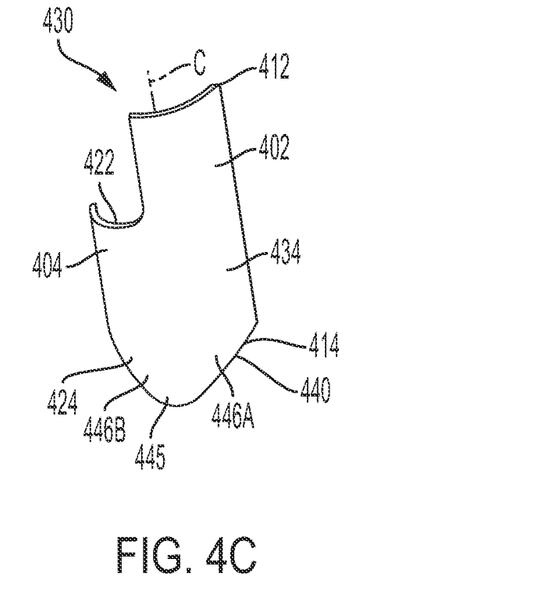
FIG. 4C is a first (lateral) side perspective view that illustrates the retractor blade of FIG. 4A.
Figure 4D:
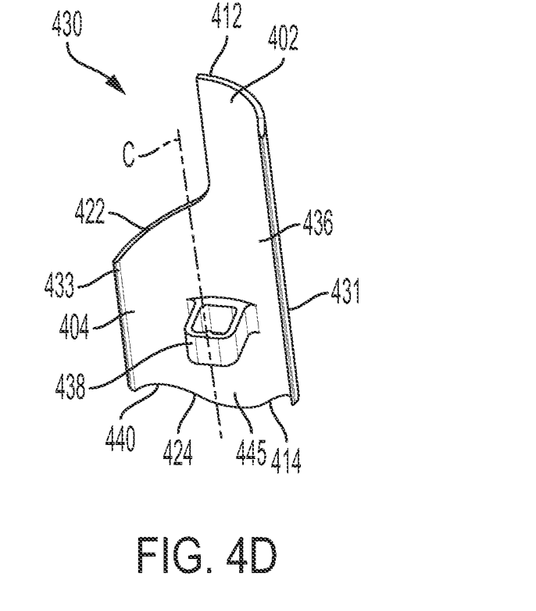
FIG. 4D is a second (medial) side perspective view that illustrates the retractor blade of FIG. 4A.

Referring now to FIGS. 4A-4D, the retractor blade 430 will be described. Specifically, FIG. 4A is a rear view that illustrates the retractor blade 430. FIG. 4B is a bottom end view that illustrates the retractor blade 430 of FIG. 4A. FIG. 4C is a first (lateral) side perspective view that illustrates the retractor blade 430 of FIG. 4A. FIG. 4D is a second (medial) side perspective view that illustrates the retractor blade 430 of FIG. 4A. Each retractor blade 430 (i.e., retractor blade 130A or 130B) may include a blade body 432 having a lateral side 434 and a medial side 436 opposite the lateral side 434. The blade body 432 may include a bottom end 440 having an inverted-arch curvature 445, as best seen in FIG. 4D. The lowest point on the inverted-arch curvature 445 may be positioned at or in proximity to the center C or a midline of the blade body 432. In some embodiments, the inverted-arch curvature 445 may be a bullet nose curvature. An inverted-arch curvature 445 or bullet nose curvature may aid the surgeon with placement into an incision. Each retractor blade 430 may include a connector 437 (i.e., connector 137 of FIG. 2B) integrated into a mid-section on the medial side 436 of the blade body 432. The connector 437 may include a leg interface 438 that may be configured to mate with a leg 182 of the distractor 180, as best seen in FIG. 2B.

Referring still to FIGS. 4A-4D, the blade body 432 may include a first body portion 402 and a second body portion 404. The first body portion 402 may include a top end 412, a bottom end 414 and a first longitudinal length between the top end and the bottom end. The second body portion 404 may include a top end 422, a bottom end 424 and a second longitudinal length that is less than the first longitudinal length between the top end 422 and the bottom end 424 of the second body portion 404. The top end 412 of the first body portion 402 may be elevated above the top end 422 of the second body portion 404.

The bottom end 414 of the first body portion 402 decreasingly slopes from a first free end 431 toward the center C or midline of the blade 430 to a first portion 446A of the inverted-arch curvature 445. The bottom end 424 of the second body portion 404 decreasingly slopes from a second free end 433 toward the center C or midline of the blade 430 to second portion 446B of the inverted-arch curvature 445. The first body portion 402 and the second body portion 404 together form a longitudinally, arch shape, as best seen in FIGS. 4A-4B. The second body portion 404 has a cutout so that the blade clears structures radiating from the tool 101. When installed, the second body portion 404 may be closest to the tool 101.

The leg interface 438 includes a band 450 having a projection 452 that may be received in the guide channel 192 (FIG. 2B) and configured to slide along the guide channel 192 to pair the projection 452 with the guide channel end 194 (FIG. 2B). In operation, the leg interface 438 may have a poka-yoke configuration so that the modular attachment and interchange of retractor blade to a distractor provides essentially an error free interchange and attachment mechanism. The poka-yoke configuration may ensure that the blade can always be attached to the distractor leg in direction of retraction. The connection of the leg 182 to the leg interface 448 may be a non-rotational connection. The shaft section 188 of the leg 182 has a square cross-section. As best seen in FIG. 4B, the interior orifice 455 of the leg interface 448 may be essentially square shaped.

Figure 5:
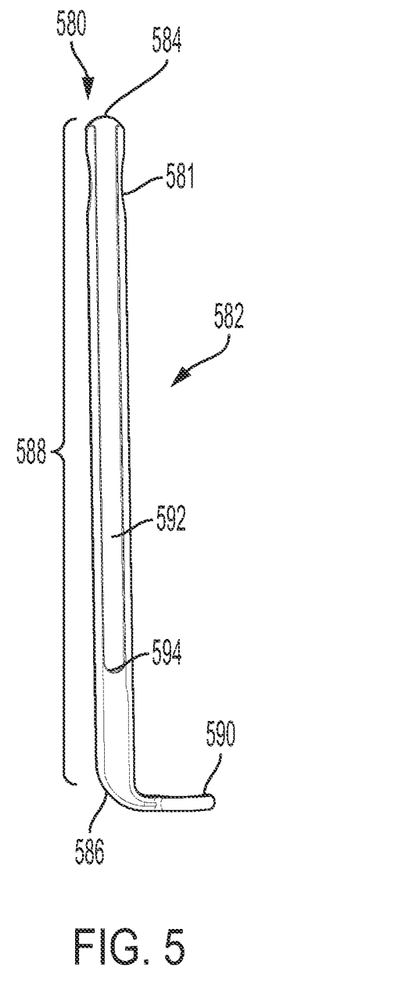
FIG. 5 is a side view that illustrates the distractor.

FIG. 5 is a side view that illustrates a distractor 580 (i.e., distractor 180A or 180B). The leg 582 (i.e., leg 182) may have a first distal end 584 and a second distal end 586 with a shaft section 588 between the first distal end 584 and second distal end 586. The distractor 580 may include a hook 590 (i.e., hook 190) at the second distal end 586 of the leg 582. The leg 582 has a longitudinal length and may include a guide channel 592 formed along a portion of the longitudinal length. The guide channel 592 may include a guide channel end 594. In the illustration, the hook 590 may be integrated with the second distal end 586 and the hook may be generally 90° relative to a longitudinal axis of the leg to orient a center of the hook opening generally parallel to the longitudinal axis. The distractor 580 may include concaved elements 581 for the placement of fingers or a thumb. The concaved elements 581 may be diametrically opposing each other on the distractor leg 582. In various embodiments, the leg 582 has a square shape. The guide channel 592 may be on a first side of the leg while the concaved elements 581 may be on sides that are essentially perpendicular to the side of the guide channel 592. In various embodiments, the leg 592 may include two guide channels 592 that are diametrically opposing each other.

Figure 6:
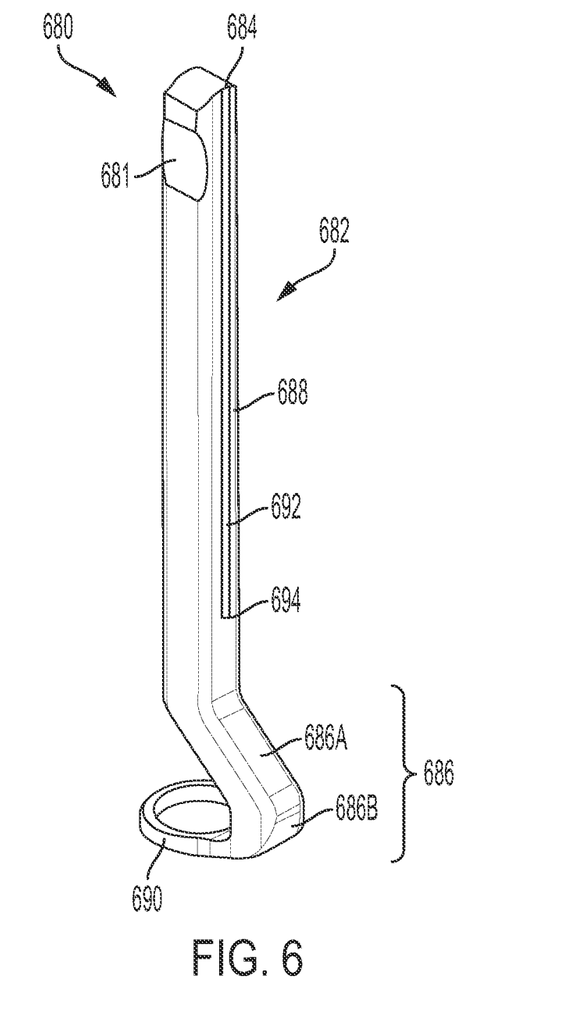
FIG. 6 is a perspective view that illustrates another distractor.

In FIG. 6, the distractor 680 may include a leg 682 having a shaft section 688 having a first distal end 684 and a second distal end 686. The distractor 580 may include a hook or eyelet 690 at the second distal end 686 of the leg 682. The leg 682 has a longitudinal length and may include a guide channel 692 formed along a portion of the longitudinal length. The guide channel 692 may include a guide channel end 694. In the illustration, the hook or eyelet 690 may be integrated with the second distal end 686. The second distal end 686 includes a first angled portion 686A that may form an obtuse angle with the longitudinal axis of the shaft section 688. The second distal end 686 includes a second angled portion 686B that may form a straight portion that may be generally parallel with the longitudinal axis of the shaft section 688 but offset. The center of the hook or eyelet 690 may be parallel to the longitudinal axis of the shaft section 688.

The distractor 680 may include at least one concaved element 681 for the placement of fingers or a thumb. In various embodiments, the leg 682 has a square shape. However, other geometric shapes may be used. The guide channel 692 may be on a first side of the leg while the concaved element 681 may be on a side that are essentially perpendicular to the side of the guide channel 692. The distractor may be configured to different hook shape or eyelet shapes.

The hook 590 or hook/eyelet 690 may have an opening which may be positioned in a plane below the bottom end 440 (FIGS. 4A and 4C-4D) of the blade or proximal the lowest point of the inverted-arch curvature.

Figure 7A:
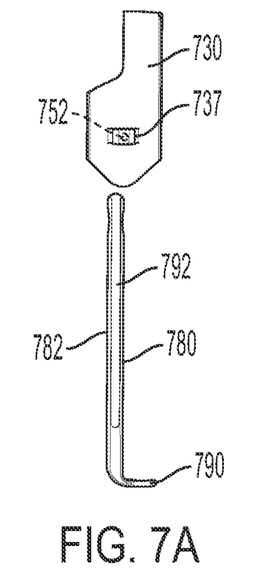
FIGS. 7A-7D are perspective second (medial) side views that illustrate steps for assembling the components of the modular surgical instrument system.
Figure 7B:
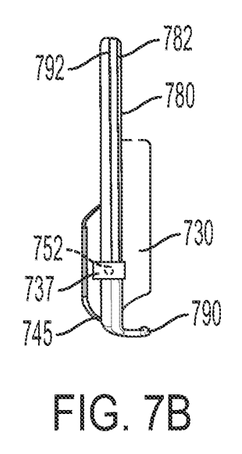

FIGS. 7A-7D are perspective side views that illustrate steps for assembling the components of the modular surgical instrument system. FIGS. 7A-7B illustrate the steps for pairing a respective one retractor blade 730 with a respective one distractor 780. The projection 752, shown in phantom, may be received in the guide channel 792 of the leg 782. The projection 752 may slide down or along the guide channel 792 to the guide channel end (not shown). This may orient the hook 790 at a plane below or proximal the lowest point of the inverted-arch curvature 745 and in a direction toward the bottom end 414 (FIGS. 4C-4D) of the first body portion 402 (FIGS. 4C-4D). The leg interface (i.e., connector 737) may be a docking stop member to stop a docking motion of the hollow tubular member 714 that is being docked onto the leg 782 of the distractor 780.

Figure 7C:
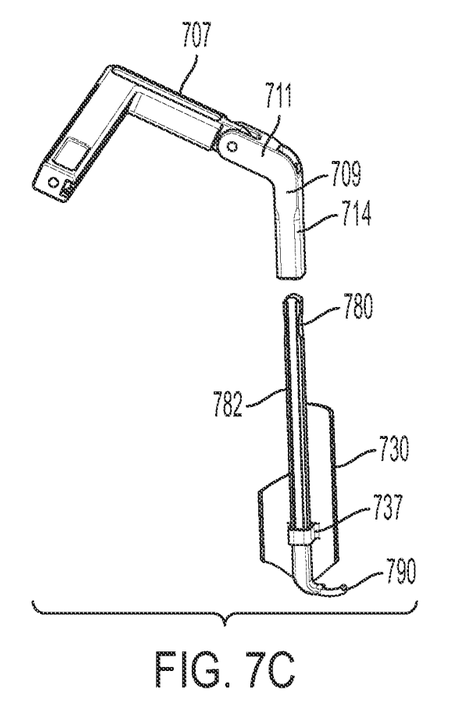
Figure 7D:
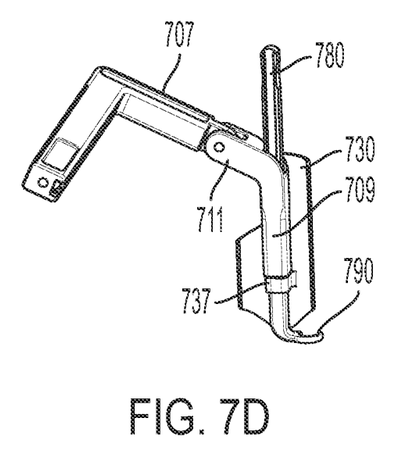
Figure 8:
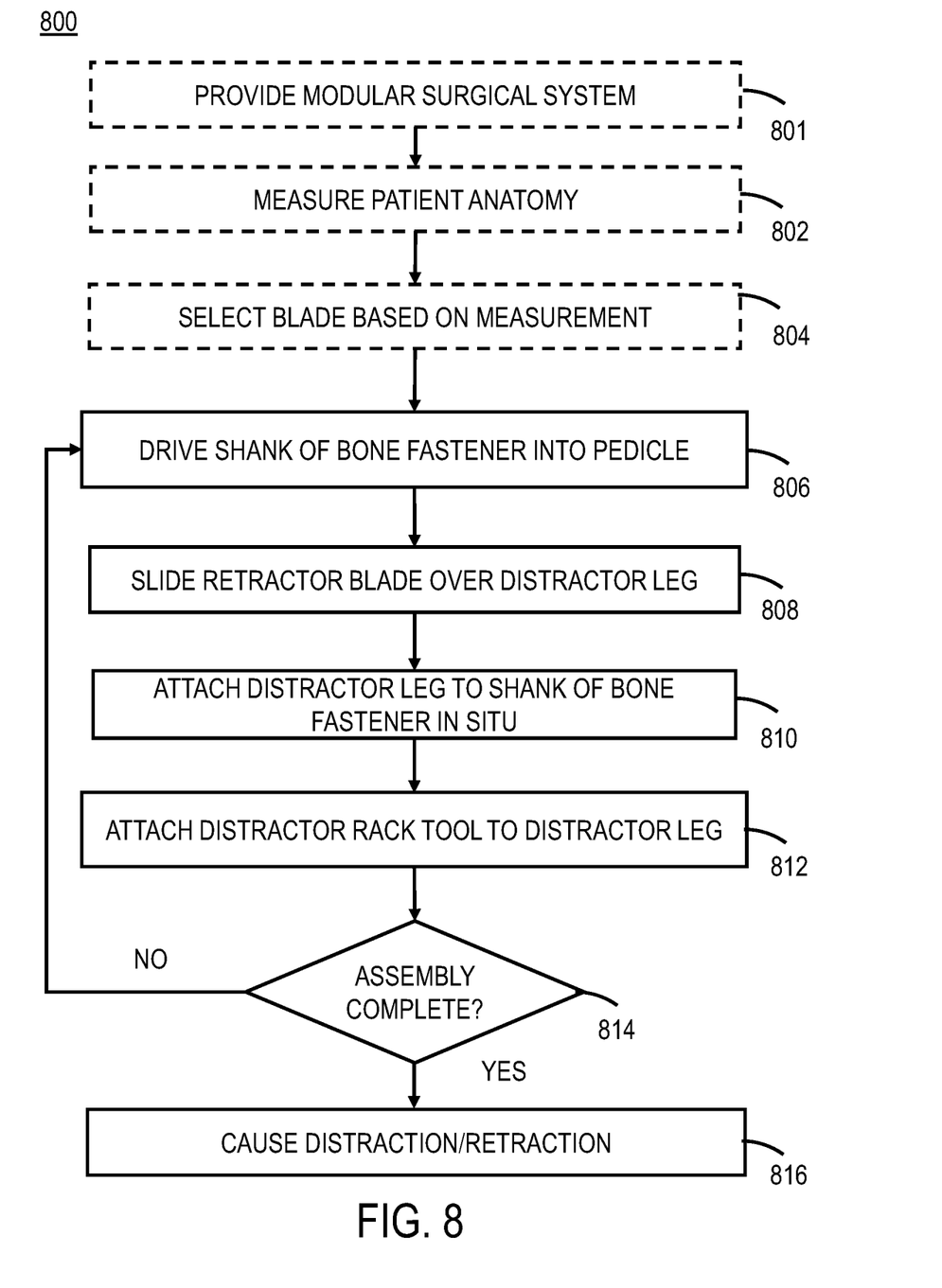
FIG. 8 is a flowchart that illustrates a method of retracting and distracting with the system of FIG. 1A.

FIG. 8 is a flowchart that illustrates a method 800 of retracting and distracting with the system 100 of FIG. 1A. The method 800 will be described in relation to FIGS. 1A-1B and 7A-7D. The method steps may be performed in the order shown or a different order. One or more of the steps may be performs contemporaneously. Furthermore, one or more steps may be added or omitted in an iteration. An example, application of the system 100 for the treatment of the spine is described in "MAST QUADRANT® Unilateral and Bilateral Techniques," by Medtronic Safemor Danek USA, Inc., copyright date 2006, and incorporated herein by reference in its entirety.

At 801, the method 800 may include providing and/or using the system 100. At 802, the patient's anatomy, such as the spine or portions of the boney structures of the spine may be measured. In some embodiments, measurement associated with a patient's height and weight may be used. The measurements of the spine or boney structures may be made using medical imaging devices, such as without limitation, a magnetic resonance imaging (MRI) device, electromagnetic radiation device or X-ray device, computed tomography (CT) scan device and/or manual surgical measuring tools. At 804, the blade for the size of the anatomy of the patient may be selected. The order of steps 801, 802 and 804 may be varied. Step 802 may be performed during surgery or as pre-operative testing and/or measuring. In some embodiments, the selection of the blade at 804 may be performed during surgery or during a surgery planning phase.

At 806, the method 800 may include driving a shank of a bone fastener into a (first) pedicle. In some embodiments, the implantation of the bone fastener may have taken place using a different surgery or the same surgery and other surgical tools, such as without limitation, those described in "MAST QUADRANT® Unilateral and Bilateral Techniques," by Medtronic Safemor Danek USA, Inc., copyright date 2006. At 808, the method 800 may include sliding a retractor blade 730 or over a distractor leg 782 of a distractor 780 to pair the retractor blade 730 and distractor 780 together, as best seen in FIGS. 7A-7B. At 808, the sliding the retractor blade 130 over the distractor leg 182 to pair the retractor blade 130 and the distractor 180 together may include orienting a distractor hook 790 at a plane below or proximal the lowest point of an inverted-arch curvature of the retractor blade 730, as best seen in FIG. 7B.

At 810, the method 800 may include attaching in situ, the distractor 780 to the shank of the bone fastener. At 812, the method 800 may include attaching a medial-lateral distractor rack tool 101 (FIG. 1A-1B) to the distractor leg 782 to assemble the system 100, as best seen in FIGS. 7C-7D. At 812, the attaching the medial-lateral distractor rack tool 101 may include docking a leg-docking member 709 of the medial-lateral distractor rack tool 101 to the distractor leg 782, as shown in FIG. 7C-7D.

At 816, the method 800 may include performing distraction and retraction with the assembled system 100 using the paired retractor blade 730 and the distractor 780. The modular surgical device 120A (FIG. 1A-1B) may be used with a retraction blade and distractor pair for both shank-based retraction and distraction and related methods of use that can be create a distraction in the disc space while retracting fascia and/or muscles during spine surgery.

The system 100 may include a second retractor blade (i.e., 130B) and second distractor (i.e., 180B) pair that need pairing and attachment to the tool 101. Accordingly, steps 806, 808, 810, and 812 may be repeated, for example. The method may include using another bone fastener.

At 814, a determination may be made whether the assembly of the system 100 is complete. If the determination is "YES," the method 800 continues to step 816. If the determination is "NO," the method 800 may include repeating steps 806, 808, 810, and 812 using a second bone fastener to be driven into a second pedicle or portion of the boney structures of the spine in proximity to the first pedicle, at 806. In such an instance, at 808, the method 800 may include sliding a second retractor blade 130B over a second distractor leg 182 of a second distractor 180B to pair the second retractor blade 130B and second distractor 180B, in the same manner as described and shown in relation FIGS. 7A-7B. In various embodiments, at 808, the sliding the second retractor blade 130B over the second distractor leg 182 to pair the second retractor blade 130B and the second distractor 180B together may include orienting a distractor hook 190 at a plane below or proximal the lowest point of an inverted-arch curvature of the retractor blade 130B, as best seen in FIG. 7B.

At 810, the method 800 may include attaching in situ, the second distractor 180B to the second shank of the second bone fastener. At 812, the method 800 may include attaching the medial-lateral distractor rack tool 101 to the second distractor leg 182 to assemble the system 100, in a similar manner as described and shown in relation to FIGS. 7C-7D. At 816, the method 800 may include performing distraction and retraction with the assembled system 100 using the paired second retractor blade 130 and the second distractor 180.

In various embodiments, at 812, the attaching of the medial-lateral distractor rack tool 101 to the second distractor leg 182 may include docking a second leg-docking member 109B of the medial-lateral distractor rack tool 101 to the second distractor leg 182, in a similar manner as described and shown in relation to FIGS. 7C-7D.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:
1. A surgical device, comprising:
at least one retractor blade comprising:
a blade body having a lateral side, a medial side opposite the lateral side, and a bottom end having an inverted-arch curvature including a lowest point in proximity to a midline of the blade body; and a connector integrated into a mid-section on the medial side of the blade body and including a leg interface configured to mate with a leg of a distractor,
wherein the distractor comprises a hook at a distal end of the leg.

2. The surgical device of claim 1,
wherein the distractor and a respective one retractor blade form a distractor/retractor pair.

3. The surgical device of claim 2, wherein:
the leg has a longitudinal length and comprises a guide channel formed along a portion of the longitudinal length;
the guide channel comprises a guide channel end; and
the leg interface includes a projection configured to be received in the guide channel and configured to slide along the guide channel to pair the projection with the guide channel end.

4. The surgical device of claim 3, wherein the leg interface provides a non-rotational connection to the leg of the distractor.

5. The surgical device of claim 3, wherein pairing of the projection to the guide channel end orients the hook proximal the lowest point of the inverted-arch curvature.

6. The surgical device of claim 1, wherein the blade body further comprises:
a first body portion comprising a top end, a bottom end and a first longitudinal length between the top end and the bottom end; and
a second body portion comprising a top end, a bottom end and a second longitudinal length which is less than the first longitudinal length between the top end and the bottom end of the second body portion,
wherein the top end of the first body portion is elevated relative to the top end of the second body portion.

7. The surgical device of claim 6, wherein:
the bottom end of the first body portion decreasingly slopes from a first free end toward the midline of the blade body to a first portion of the inverted-arch curvature; and
the bottom end of the second body portion decreasingly slopes from a second free end toward the midline of the blade body to a second portion of the inverted-arch curvature.

8. A modular surgical instrument system comprising:
a medial-lateral distractor rack tool having first and second parallel arms;
first and second leg-docking members connected to the first and second parallel arms;
a first distractor having a first distractor leg comprising a hook at a distal end thereof, the second distractor leg being configured to be docked with the first leg-docking member;
a second distractor having a second distractor leg comprising a hook at a distal end thereof, the second distractor leg being configured to be docked with the second leg-docking member; and
a retractor blade pair, each retractor blade of the blade pair comprises:
a blade body having a lateral side, a medial side opposite the lateral side and a bottom end having an inverted-arch curvature including a lowest point in proximity to a midline of the blade body, and
a connector integrated into a mid-section on the medial side of the blade body and including a leg interface configured to mate with the first distractor leg or the second distractor leg.

9. The modular surgical instrument system of claim 8, wherein each of the first and second leg-docking members comprises:
a yoke;
a connector pin configured to connect to a respective one arm of the first and second parallel arms; and
a hollow tubular member having a first end integrated with the yoke and a second end opposite the first end, wherein the yoke is arranged at an angle relative to the first end of the hollow tubular member.

10. The modular surgical instrument system of claim 9, wherein:
each distractor leg, of the first and second distractor legs, has a longitudinal length and comprises a guide channel formed along a portion of the longitudinal length;
the guide channel comprises a guide channel end;
the leg interface includes a projection configured to be received in the guide channel and configured to slide along the guide channel to pair the projection with the guide channel end; and
the leg interface is a docking stop member to stop a docking motion of the hollow tubular member being docked.

11. The modular surgical instrument system of claim 10, wherein pairing of the projection to the guide channel end orients the hook of the first distractor or the hook of the second distractor proximal the lowest point of the inverted-arch curvature.

12. The modular surgical instrument system of claim 8, wherein the blade body further comprises:
a first body portion comprising a top end, a bottom end and a first longitudinal length between the top end and the bottom end; and
a second body portion comprising a top end, a bottom end and a second longitudinal length which is less than the first longitudinal length between the top end and the bottom end of the second body portion,
wherein the top end of the first body portion is elevated above the top end of the second body portion and the first body portion and the second body portion together form a longitudinally, arch shape.

13. The modular surgical instrument system of claim 12, wherein:
the bottom end of the first body portion decreasingly slopes from a first free end toward the midline of the blade body to a first curvature portion of the inverted-arch curvature; and
the bottom end of the second body portion decreasingly slopes from a second free end toward the midline of the blade body to a second curvature portion of the inverted-arch curvature.

14. The modular surgical instrument system of claim 8, wherein the retractor blade pair comprises a first retractor blade and a second retractor blade being a mirror image of the first retractor blade.

15. A method, comprising:
providing a modular surgical instrument system comprising:
a medial-lateral distractor rack tool having first and second parallel arms;
first and second leg-docking members connected to the first and second parallel arms;
a first distractor having a first distractor leg configured to be docked with the first leg-docking member;
a second distractor having a second distractor leg configured to be docked with the second leg-docking member; and a retractor blade pair, each retractor blade of the blade pair comprises:
   a blade body having a lateral side, a medial side opposite the lateral side and a bottom end having an inverted-arch curvature including a lowest point in proximity to a midline of the blade body, and
      a connector integrated into a mid-section on the medial side of the blade body and including a leg interface configured to mate with the first distractor leg or the second distractor leg;
driving a shank of a bone fastener into a pedicle;
sliding a retractor blade over a distractor leg of a distractor to pair the retractor blade and distractor together;
attaching in situ, the distractor to the shank of the bone fastener;
attaching a medial-lateral distractor rack tool to the distractor leg to assemble the system; and
performing distraction and retraction with the assembled system using the paired retractor blade and the distractor.

16. The method of claim 15, wherein the attaching the medial-lateral distractor rack tool comprises:
   docking a leg-docking member of the medial-lateral distractor rack tool to the distractor leg.

17. The method of claim 15, wherein the sliding the retractor blade over the distractor leg to pair the retractor blade and the distractor together comprises:
   orienting a distractor hook proximal the lowest point of an inverted-arch curvature of the retractor blade.

18. The method of claim 15, further comprising:
   driving a second shank of a second bone fastener into a second pedicle;
   sliding a second retractor blade over a second distractor leg of a second distractor to pair the second retractor blade and second distractor;
   attaching in situ, the second distractor to the second shank of the second bone fastener;
   attaching the medial-lateral distractor rack tool to the second distractor leg to assemble the system; and
   performing distraction and retraction with the assembled system using the paired second retractor blade and the second distractor.

19. The method of claim 18, wherein the attaching the medial-lateral distractor rack tool to the second distractor leg comprises:
   docking a second leg-docking member of the medial-lateral distractor rack tool to the second distractor leg.

20. The method of claim 18, wherein the sliding the second retractor blade over the second distractor leg to pair the second retractor blade and the second distractor together comprises:
   orienting a distractor hook proximal the lowest point of an inverted-arch curvature of the retractor blade.

* * * * *